United States Patent
Dinkler, II et al.

(12) United States Patent (10) Patent No.: US 7,232,411 B2
(45) Date of Patent: Jun. 19, 2007

(54) RADIOLUCENT RETRACTOR AND RELATED COMPONENTS

(75) Inventors: Charles E. Dinkler, II, Cincinnati, OH (US); Kevin R. Easton, Cincinnati, OH (US); Ali Mowlai-Ashtiani, Jacksonville, FL (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 214 days.

(21) Appl. No.: 10/476,596

(22) PCT Filed: Apr. 19, 2002

(86) PCT No.: PCT/US02/12513

§ 371 (c)(1),
(2), (4) Date: Nov. 22, 2004

(87) PCT Pub. No.: WO02/085187

PCT Pub. Date: Oct. 31, 2002

(65) Prior Publication Data

US 2005/0080319 A1 Apr. 14, 2005

Related U.S. Application Data (60) Provisional application No. 60/285,257, filed on Apr. 20, 2001.

(51) Int. Cl.
*A61B 17/02* (2006.01)

(52) U.S. Cl. .................... 600/233; 600/230

(58) Field of Classification Search .......... 600/227, 600/228, 229, 230, 231, 232, 233; 403/76, 403/90, 263
See application file for complete search history.

(56) References Cited

U.S. PATENT DOCUMENTS

| 4,312,336 A | * | 1/1982 | Danieletto et al. ........... 606/57 |
| 4,457,300 A |   | 7/1984 | Budde |
| 4,615,072 A | * | 10/1986 | Lautenschlager, Jr. ....... 16/238 |
| 4,803,976 A |   | 2/1989 | Frigg et al. |
| 5,284,129 A | * | 2/1994 | Agbodoe et al. ........... 600/230 |
| 5,529,358 A |   | 6/1996 | Dinkler et al. |

(Continued)

OTHER PUBLICATIONS

International Search Report for Applicant's PCT Application No. PCT/US02/12513, Aug. 9, 2002, ISA/US.

*Primary Examiner*—Cary E. O'Connor
(74) *Attorney, Agent, or Firm*—Wood, Herron & Evans, L.L.P.

(57) ABSTRACT

A radiolucent halo-type retractor (20) having a radiolucent curvilinear fixed member (32) connected to a radiolucent curvilinear movable member (34). Each of the fixed and movable members has a radiolucent male coupling (44, 46) projecting outward from a convex surface (40, 42) to receive a female coupling of a retractor arm. The ends (60, 68) of the movable member are separated by a distance less than a distance separating the ends (56, 64) of the fixed member. Radiolucent starburst connectors (58, 62) are disposed on first ends of the fixed and movable members to secure the fixed and movable members at a desired angular orientation. Radiolucent starburst connectors (66, 70) are also disposed on second ends of the fixed and movable members to secure the fixed and movable members at a desired angular orientation. A pin (72) rotatably connects the first ends. A locking shaft (76) rotatably connects the second ends and is operable to lock the fixed and movable members in a desired orientation.

30 Claims, 5 Drawing Sheets

U.S. PATENT DOCUMENTS

| | | |
|---|---|---|
| 5,630,805 A | 5/1997 | Ternamian |
| 5,722,978 A | 3/1998 | Jenkins, Jr. |
| 6,129,729 A | 10/2000 | Snyder |
| 6,198,961 B1 | 3/2001 | Stern et al. |

* cited by examiner

RADIOLUCENT RETRACTOR AND RELATED COMPONENTS

This application is a 371 of International Patent Application No. PCT/US02/12513, filed on Apr. 19, 2002, which claims priority to Provisional Application Ser. No. 60/285,257, filed on Apr. 20, 2001, both hereby expressly incorporated by reference herein.

FIELD OF THE INVENTION

This invention relates generally to the field of surgical instruments, and more particularly, to a halo-style surgical retractor to facilitate holding bodily tissues, membranes, and vessels, retracted during cranial surgery.

BACKGROUND OF THE INVENTION

There are many different known surgical retractor components, for example, halo-style retractors and supporting components as well as flexible retractor arms. Halo-style retractors are often made of two hinged, generally semicircular half-rings, a first of which is affixed to supporting structure. A second half-ring is pivotable and adjustable with respect to the first half-ring about a generally diametric axis of rotation. Retractor arms and other attachments are attachable to the half-rings via an internal dovetail slot extending along an outer directed surface of the half-rings. The halo-style retractor is mounted on a cranial stabilization device, for example, a skull clamp, and its position and orientation are adjustable to meet the needs of the surgical procedure. Often the skull clamp is radiolucent and may, in turn, be mounted on a radiolucent patient support structure such as an operating table extension.

The components of such halo-style retractors are usually fabricated from stainless steel or other metals. One problem with such halo-style retractors is that the metal is radiopaque to x-ray and other imaging processes, and such metal parts produce "artifacts" in resulting images. These artifacts diminish the usefulness of the imaging process because they often obscure an image of a portion of a patient that normally would be viewable, absent the obscuring radiopaque retractor arm, halo-type retractor and supporting components. Further, more and more surgical procedures are requiring interoperative scanning procedures, and the use of radiopaque retractor components complicates such procedures. For example, one option is to remove the radiopaque equipment prior to the scanning process. As will be appreciated, that option is not often possible in an interoperative procedure. Another option is to position and orient the radiopaque retractor components so that they still provide the desired surgical function but also minimize artifacts and interference in portions of a scanned image that are of interest to a surgeon. This option is at best, difficult, time consuming and provides only a limited benefit, and at worst, the option is practically not available.

Therefore, there is a need for a radiolucent retractor arm, a radiolucent halo-type surgical retractor and a radiolucent retractor support structure that minimize artifacts in an imaging process.

SUMMARY OF THE INVENTION

The present invention provides a radiolucent flexible retractor arm, radiolucent halo-style retractor and radiolucent support structure that produce minimal artifacts in an images. The radiolucent retractor components of the present invention are especially beneficial when used with interoperative scanning procedures. Further, the radiolucent halo-style retractor of the present invention uses minimal parts, is cost effective to manufacture and easy to use.

According to the principles of the present invention and in accordance with the described embodiments, the invention provides a radiolucent halo-type retractor having a radiolucent curvilinear fixed member and a radiolucent movable member. Each of the fixed and movable members has a radiolucent male coupling projecting radially outward from a convex surface on the respective fixed and movable members. Further, a pin rotatably connects respective first ends of the fixed and movable members; and a locking shaft rotatably connects respective second ends of the fixed and movable members. The locking shaft is operable to lock the fixed and movable members in a desired relative orientation. The application of male coupling members to the fixed and movable members substantially simplifies the process of molding the fixed and movable members and thus, helps to reduce the cost of manufacturing the members.

In another embodiment of the invention, a radiolucent halo-type retractor has a radiolucent curvilinear fixed member and a radiolucent curvilinear movable member. First and second radiolucent starburst connectors are disposed on first ends of the fixed and movable members respectively. The first and second starburst connectors secure the first ends of the fixed and movable members at a desired relative angular orientation. Third and fourth radiolucent starburst connectors are disposed on second ends of the fixed and movable members, respectively. The third and fourth starburst connectors secure the second ends of the fixed and movable members at a desired relative angular orientation. A radiolucent pin is affixed to one of the first and second starburst connectors and extends through another of the first and second starburst connectors. The pin providing an axis of rotation for the first ends of the fixed and movable members. A radiolucent locking shaft is mounted with respect to one of the third and fourth starburst connectors and threadedly engages another of the third and fourth starburst connectors. The locking shaft provides an axis of rotation for the second ends of the fixed and movable members. The use of the four starburst connectors on the overlapping ends of the fixed and movable members simplifies the structure of the retractor without compromising its rigidity when the members are locked together.

In a further embodiment of the invention, a radiolucent halo-type retractor has a radiolucent curvilinear fixed member and a radiolucent curvilinear movable member. First and second ends of the fixed member are separated by a distance different from a distance separating first and second ends of the movable member. A first pin rotatably connects the first ends of the fixed and movable members, and a locking shaft rotatably connects the second ends of the fixed and movable members. The locking shaft is operable to lock the fixed and movable members in a desired relative orientation.

In one aspect of this invention, the distance separating the ends of the movable member is less than the distance separating the ends of the fixed member. Therefore, upon the locking shaft locking the fixed and movable members together, the movable member resiliently spreads and the distance between the first and second ends of the movable member becomes substantially equal to the distance between the first and the second ends of the fixed member. Such a construction permits the movable member to be controlled by loosening a single locking shaft. Further, the resiliency of the movable member allows the surgeon to "feel" the motion of the movable member as it "clicks" or "snaps" from one starburst tooth to another, and thus, the surgical retractor is substantially easier to use than known halo-style retractors. In addition, the capability of being able to adjust and lock the movable member with respect to the fixed member is accomplished with only one additional part, the locking shaft. This reduction in parts from known halo-style retractors also helps to reduce the manufacturing cost and provides a more reliable and trouble free operation.

These and other advantageous features of the invention will be more readily understood in view of the following detailed description of the preferred embodiment and the drawings.

DETAILED DESCRIPTION OF THE INVENTION

Figure 1:
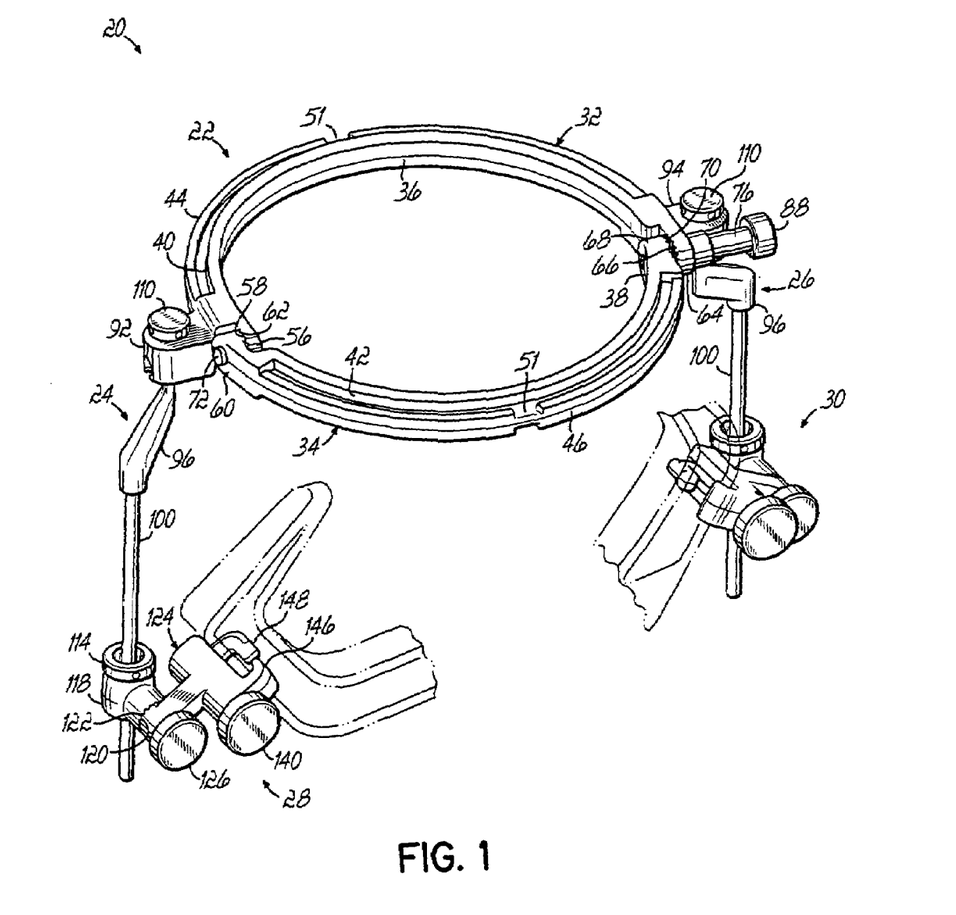
FIG. 1 is a perspective view of a radiolucent halo-style retractor with a radiolucent support bracket and radiolucent mounting clamp in accordance with the principles of the present invention.
Figure 2:
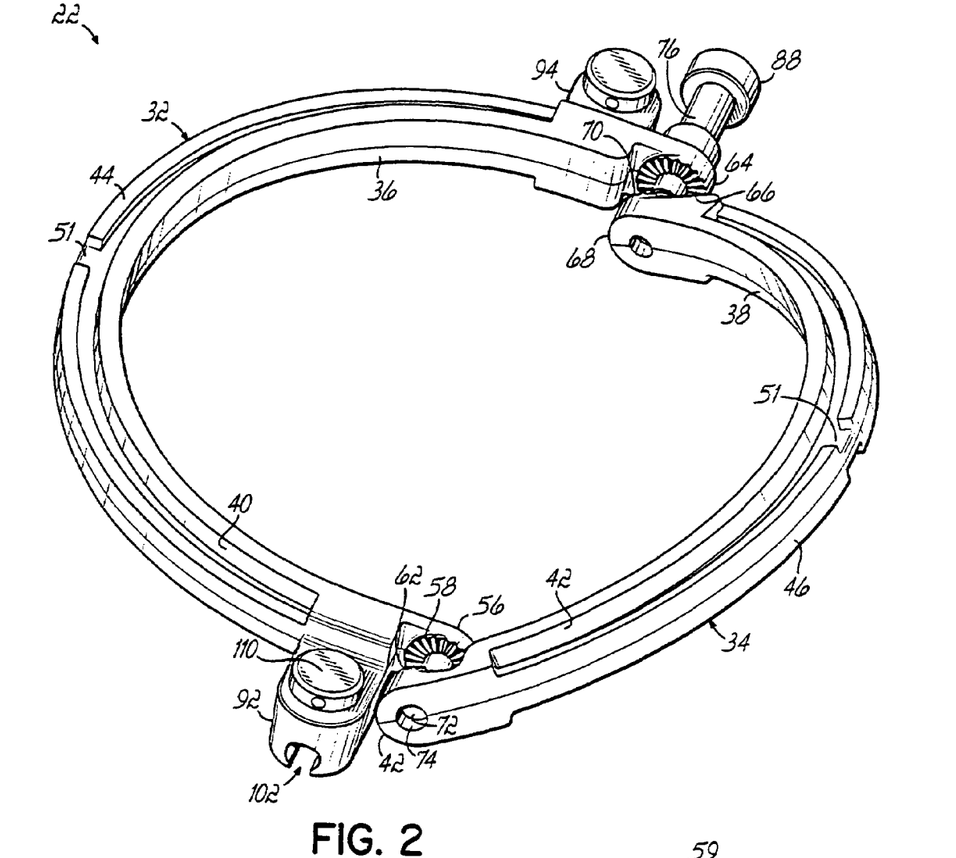
FIG. 2 is a perspective view of the halo-style retractor arm of FIG. 1 without the flexible retractor arm and support bracket.

Referring to FIG. 1, a radiolucent, halo-style surgical retractor 20 is comprised of a radiolucent retractor ring 22 that is mounted on upper ends of radiolucent support brackets 24, 26. The support brackets are, in turn, mounted at their lower ends to radiolucent mounting clamps 28, 30. The retractor ring 22 is comprised of a radiolucent, curvilinear fixed member or half-ring 32 and a radiolucent, curvilinear movable member or half-ring 34. As shown in FIG. 2, the fixed and movable members 32, 34 have respective inner concave surfaces 36, 38 and respective outer convex surfaces 40, 42. Further, the fixed and movable members 32, 34 have respective radiolucent male couplings 44, 46 projecting radially outward from the respective convex surfaces 40, 42. The male couplings 44, 46 are substantially identical in construction and cross-sectional profile.

Figure 4:
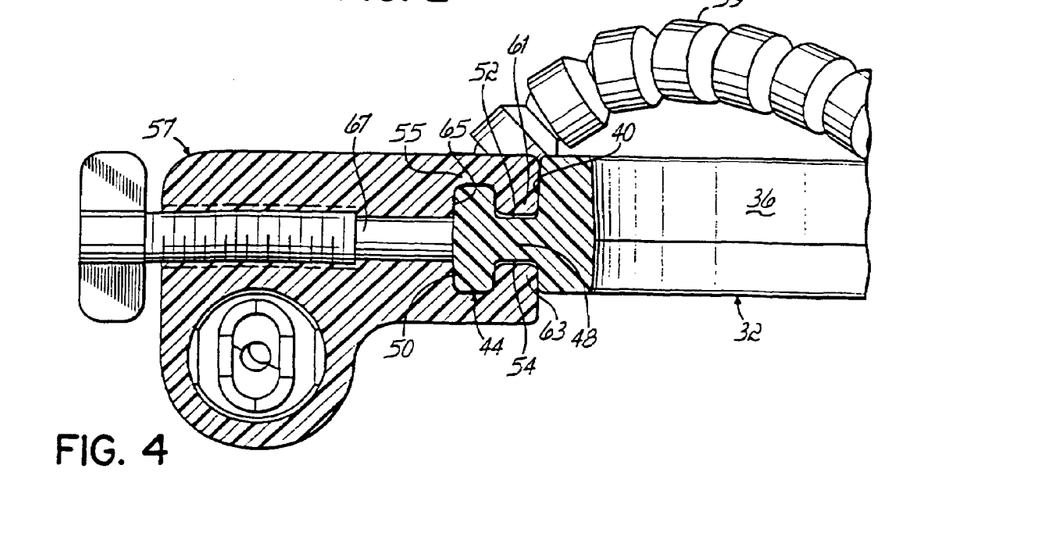
FIG. 4 is a cross-sectional view taken along line 4—4 of FIG. 3 and illustrates the mounting of the retractor arm on the halo-style retractor of FIG. 1.

Referring to FIG. 4, the male coupling 44 has a radiolucent, curvilinear leg 48 with an inner or proximal end connected to the convex surface 40. An outer or distal end of the leg 48 is connected to a radiolucent, curvilinear locking member 50. The male coupling 44 forms curvilinear opposed upper and lower channels 52, 54, respectively. Thus, the male coupling 44 is capable of receiving a female coupling 55 of a holder 57 for a retractor blade or arm 59.

The female coupling 55 has respective upper and lower projections 61, 63 that extend into the respective channels 52, 54, and the female coupling 55 has an internal opening 65 that has a cross-sectional profile shaped and sized to slidingly receive the locking member 50. The holder 57 is secured on the fixed member 32 by tightening a locking screw 67 that contacts an outer convex surface of the locking member 50. Referring to FIG. 2, each of the locking members 50 of the male couplings 44, 46 have a discontinuity or opening 51 that is sized to receive the female coupling 55. The openings 51 permit the holder to be mounted on a desired one of the fixed and movable members 32, 34.

Figure 3:
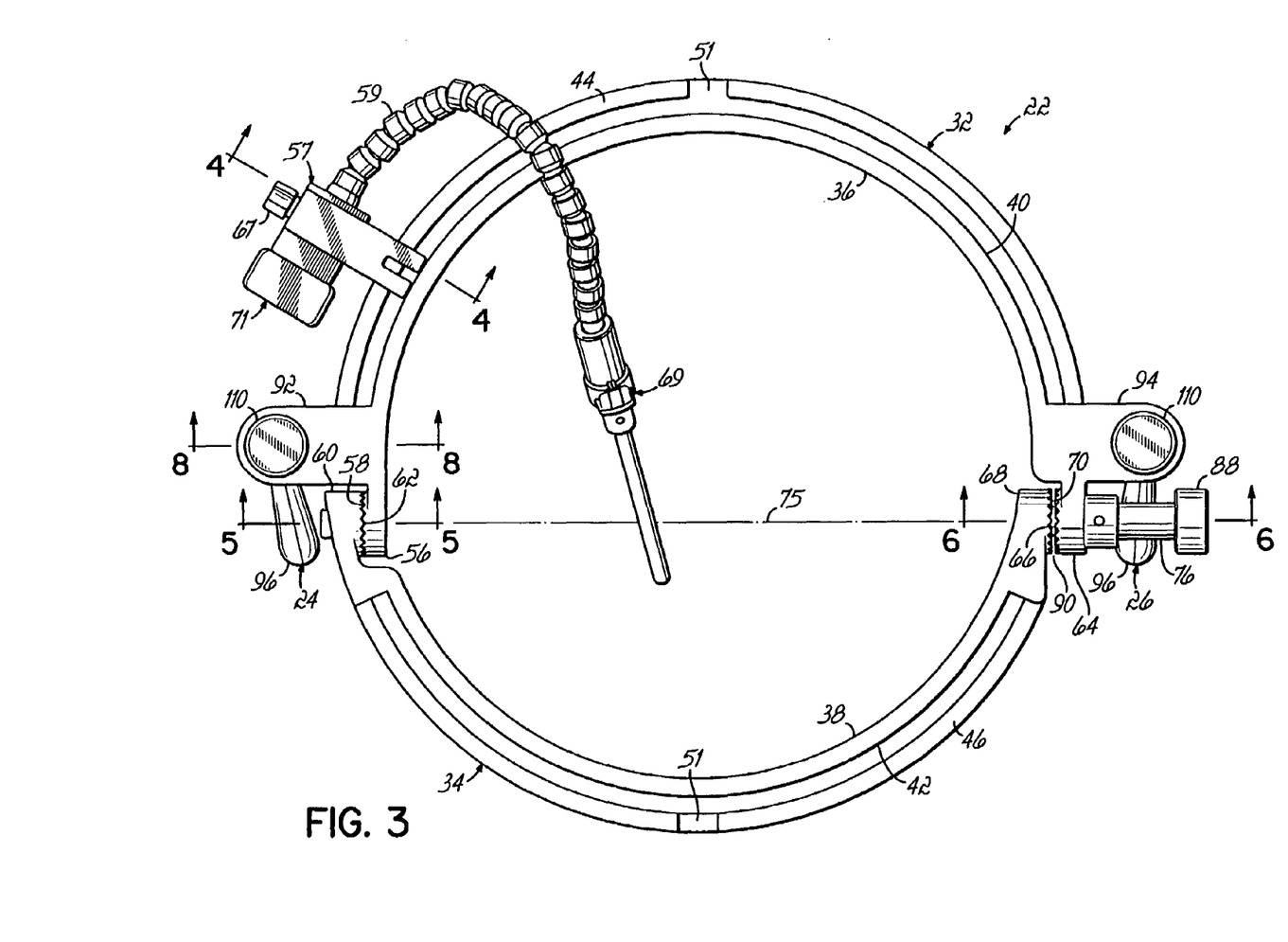
FIG. 3 is a top plan view of the halo-style retractor shown in FIG. 1 with a flexible retractor arm mounted thereon.

Referring to FIG. 3, the radiolucent fixed member 32 has a first end 56 with a radiolucent, first starburst connector 58 disposed thereon. Similarly, the radiolucent movable member 34 has a first end 60 with a radiolucent second starburst connector 62 disposed thereon. Thus, the first and second starburst connectors 58, 62 are effective to maintain the first ends 56, 60 of the respective fixed and movable members 32, 34 in a desired angular relationship. The fixed member 32 has a second end 64 with a radiolucent third connector 66 disposed thereon, and the movable member 34 has a second end 68 with a radiolucent fourth starburst connector 70 disposed thereon. Thus, the third and fourth starburst connectors 66, 70 are effective to maintain the second ends 64, 68 of the respective fixed and movable members 32, 34 at a desired angular orientation with respect to each other.

Figure 5:
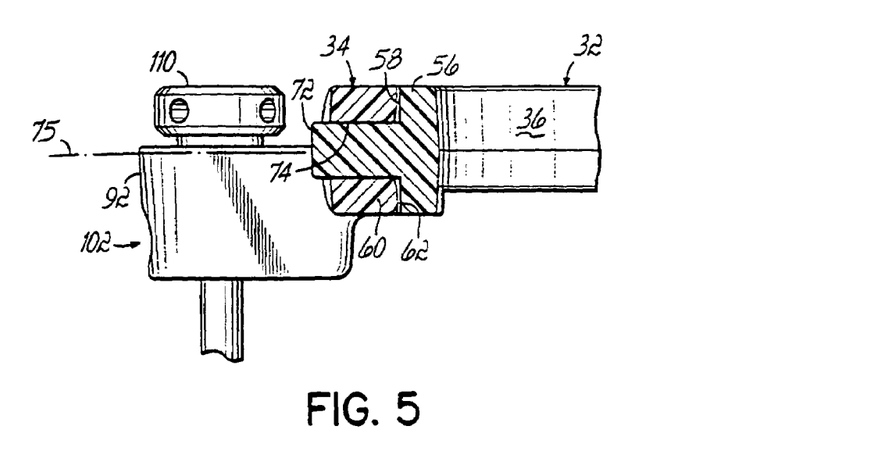
FIG. 5 is a cross-sectional view taken along the axis of rotation 75 of FIG. 3 and illustrates one connection between fixed and movable members of the halo-style retractor of FIG. 1.

Referring to FIG. 5, the first end 56 of the fixed member 32 has a radiolucent pin 72 extending therefrom. The pin 72 is disposed at a center of the first starburst connector 58 and extends through a hole 74 located at the center of the second starburst connector 62. Thus, the pin 72 provides an axis of rotation 75 between the first ends 56, 60 of the respective fixed and movable members 32, 34.

Figure 6:
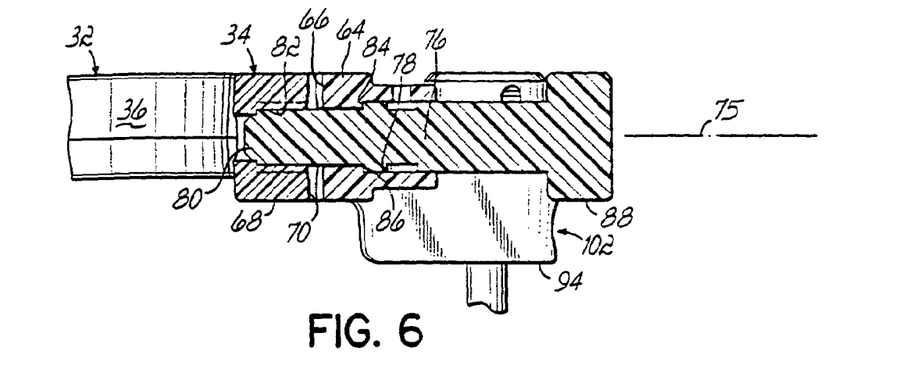
FIG. 6 is a cross-sectional view taken along the axis of rotation 75 of FIG. 3 and illustrates another connection between fixed and movable members of the halo-style retractor of FIG. 1.

Referring to FIG. 6, a radiolucent locking shaft 76 extends through a clearance hole 78 located in the center of the third starburst connector 66 on the second end 64 of the fixed member 32. The locking shaft 76 has a threaded end 80 that engages a threaded hole 82 located at the center of the fourth starburst connector 70 on the second end 68 of the movable member 34. The locking shaft 76 has a shoulder 84 that contacts a shoulder 86 adjacent the clearance hole 78 so that motion of the locking shaft 76 through the clearance hole 78 is limited. A radiolucent locking knob 88 is disposed on an opposite end of the locking shaft 76. As the user rotates the locking knob 88, the locking shaft 76 pulls the third and fourth starburst connectors 66, 70 into engagement. thereby locking the second ends 64, 68 of the respective fixed and movable members 32, 34 at a desired angular orientation.

Referring back to FIG. 3, in one embodiment, the distance between the first and second ends 56, 64 of the first member is different from the distance between the first and second ends 60, 68 of the movable member 34. In other words, the distance between the centers of the first and third starburst connectors 58, 66 is different from the distance between the centers of the second and fourth starburst connectors 62, 70. The distance between the second and fourth starburst connectors 62, 70 is less, for example, by about 0.125 inches, than the distance between the centers of the first and third starburst connectors 58, 66. Therefore, when the locking shaft 76 is loose, there is a gap or spacing 90 between the third and fourth starburst connectors 66, 70 of about 0.125 inches. As the locking shaft 76 is rotated in a locking direction, the movable member second end 64 resiliently stretches and moves toward the fixed member second end 68. That spreading or stretching of the movable member 34 brings the fourth starburst connector 70 into locking engagement with the third starburst connector 66. The spreading or stretching of the movable member 34 also forces the second starburst connector 62 against the first. starburst connector 58 via a force vector directed generally from left to right in FIG. 3 and substantially parallel to the axis of rotation 75.

When the locking shaft 76 is rotated in an opposite, unlocking direction, movable member 34 automatically returns toward its unstretched state, that is, its second end 68 automatically moves toward its first end 60. In that process, the movable member second end 68 automatically separates from the fixed member second end 64, thereby causing the fourth starburst connector 70 to disengage from the third starburst connector 66. Thus, rotating the locking shaft 76 in the unlocking direction allows the second and fourth starburst connectors 62, 70 on the movable member 34 to be rotated with respect to the first and third starburst connectors 58, 66 on the fixed member 32.

As shown in FIG. 1, the fixed member 32 has first and second radiolucent ears 92, 94, respectively, extending radially outward from the respective first and second ends 56, 64. The ears 92, 94 are used to facilitate attachment of the fixed member 32 with the respective mounting brackets 24, 26. Since the structure and operation of the mounting brackets 24, 26 and clamps 28, 30 are identical, only the structure and operation of the radiolucent support bracket 24 and radiolucent clamp 28 will be described in detail. The support bracket 24 has a radiolucent angular body 96. A radiopaque, metal ball 98 is mounted to an upper end 97 (FIGS. 7, 8) of the body 96. An upper end of a radiolucent support rod 100 is rigidly connected to a lower end of the body 96.

Figure 8:
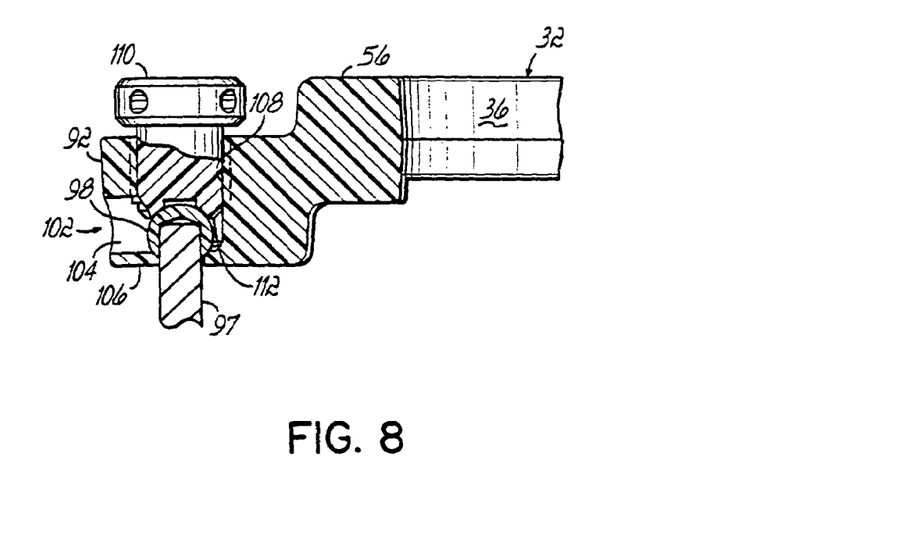
FIG. 8 is a cross-sectional view taken along line 8—8 of FIG. 3 and illustrates a connection between the support bracket and the halo-style retractor of FIG. 1.

Referring to FIGS. 2 and 8, the ear 92 has a generally key-shaped opening 102. The key-shaped opening 102 has a circular portion 104 and a slot portion 106. The circular portion 104 has a diameter larger than the diameter of the ball 98, and the slot portion 106 has a slot width greater than the diameter of the support rod 100. Thus, the support rod 100 with the ball 98 can be readily inserted into the opening 102. The ear 92 further has a threaded opening 108 with a centerline that is oriented substantially perpendicular to a centerline of the opening 102. A radiolucent locking screw 110 threadedly engages the opening 108 and has an annular end surface 112 that is shaped to tightly contact the ball 98 as the locking screw 110 is tightened. Thus, the angular orientation of the fixed member 32 is adjustable by loosening and tightening the radiolucent locking screw 110.

Referring back to FIG. 7, a lower end of the radiolucent support rod 100 is attachable to the mounting clamp 28 by extending the support rod 100 through a radiolucent compression nut 114 and a radiopaque, metal compression ball 116 disposed in a radiolucent rod holder 118. Thus, the position and orientation of the support rod 100 with respect to the clamp 28 is adjustable by tightening and loosening the compression nut 114. The rod holder 118 has a radiolucent starburst connector 120 that is engageable with a radiolucent starburst connector 122 disposed on a radiolucent fixed body 124 of the mounting clamp 28. A radiolucent locking screw 126 has a threaded end that extends through a clearance hole 128 in the center of the starburst connector 122 and threadedly engages the rod holder 118. The locking screw 126 has a circular relief slot 130. Thus, when the locking screw 126 is inserted through the clearance hole 128, the relief slot 130 aligns with a diametric throughhole 132. A radiolucent retaining pin 134 is inserted through the hole 132 and passes through the relief channel 130, thereby retaining the locking screw 126 within the fixed body 124. Thus, the angular orientation of the support rod 100 with respect to the mounting clamp 28 is adjustable by loosening and tightening the locking screw 126.

Figure 7:
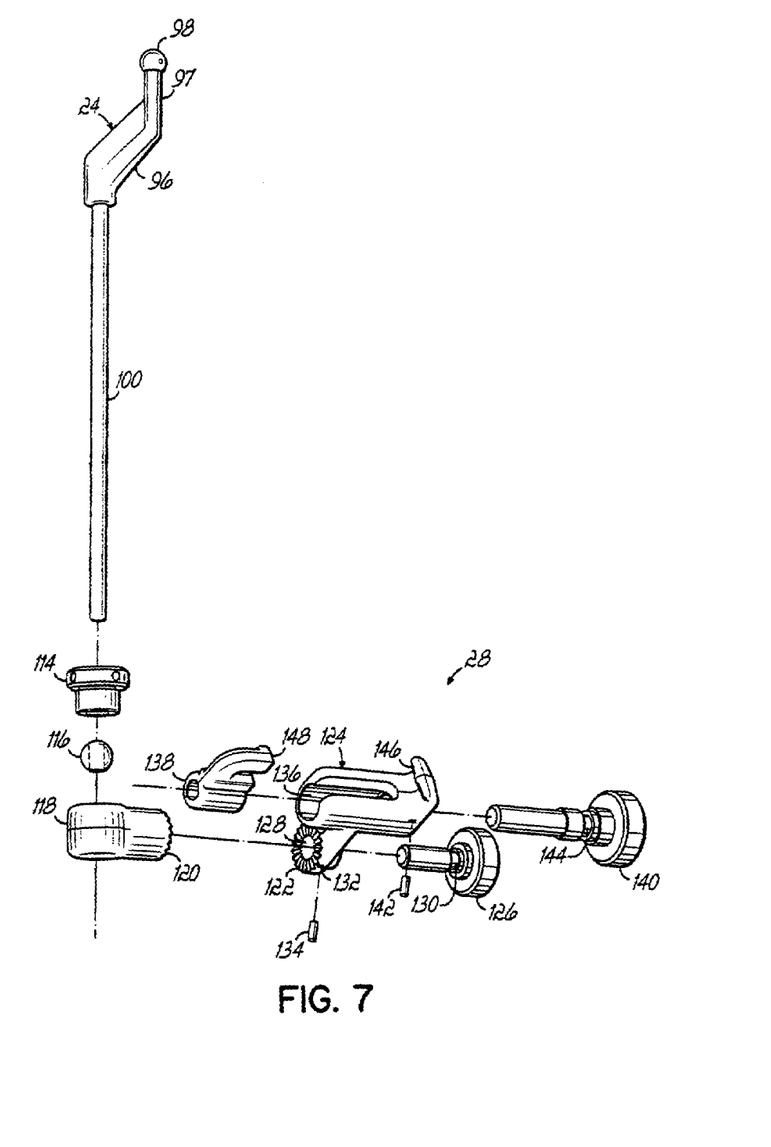
FIG. 7 is a disassembled view of the support bracket and mounting clamp used with the halo-style retractor of FIG. 1.

The radiolucent fixed body 124 has an opening 136 sized to receive a radiolucent sliding body 138. A radiolucent locking screw 140 has a threaded end that threadedly engages the sliding body 138. The locking screw 140 also has a radiolucent retaining pin 142 that extends across a circular relief slot 144, thereby retaining locking screw 140 within the fixed body 124. The fixed body 124 has a radiolucent fixed hook 146 that is opposite a radiolucent sliding hook 148 on the sliding body 138. Thus, the mounting clamp 28 can be mounted to an arm of a skull clamp by successively loosening and tightening the locking screw 140.

Except as otherwise noted, all of the parts of the halo-style retractor 20 are made of a radiolucent material, for example, a "DELRIN" acetal polymer. Other radiolucent materials may be used. The metal ball 98 and compression ball 116 are made of aluminum. The various radiolucent parts described herein can be made by machining, by molding, a combination of molding or machining or any other process compatible with the radiolucent material.

In use, the radiolucent mounting clamps 28, 30 (FIG. 1) are first attached to opposite arms of a radiolucent cranial stabilization device, for example, a radiolucent skull clamp (shown in phantom). Such a skull clamp is shown and described in U.S. Pat. No. 5,537,704 that is assigned to the assignee of the present application. Next, the support rods 100 of the support brackets 24, 26 are inserted through the rod holders 118 of the mounting clamps 28, 30. The retractor ring 22 is located at a desired height with respect to the patient's skull. Next one or more holders 57 for a retractor arm 59 or other blade holder is placed adjacent to, and slid over, the opening 51 on one of the male couplings 44, 46. The retractor arm holder 57 is then moved along the channels or paths 52, 54 to a desired location and locked in place using locking screw 67. The location and angular orientation of the fixed and movable members 32, 34 can be further adjusted by loosening and tightening the locking shaft 76 and locking screws 110.

Referring to FIG. 3, the retractor arm 59 is a disposable, radiolucent, flexible retractor arm and includes a plurality of ball and socket radiolucent pieces, which terminate in a coupling 69 located at an outer or distal end of the retractor arm 59. The coupling 69 is made by Colder Products Company and is shown in U.S. Pat. No. 5,052,725. This coupling 69 enables a retractor blade to be removably held at the distal end of the flexible retractor arm 59. Moreover, an internal string (not shown) extends along the entire length of the retractor arm 59; and at its distal end, the string is held in place at the coupling 69. At an inner or proximal end of the flexible retractable arm 69, the string is held in place via a threaded bolt and knob assembly 71, which enables the string to be tightened or loosened to reorient the position of the retractor arm 59 relative to the halo retractor 20. This enables the flexible retractor arm 59 to be repositioned relative to the head of the patient, as desired by the neurosurgeon during a neurosurgical procedure.

The radiolucent halo-style retractor 20 has several advantages over known retractors. First, it is radiolucent and substantially reduces artifacts when it is scanned in an imaging process. This is especially beneficial when the interoperative scans are taken during a surgical procedure. The radiolucent quality of the halo-type retractor, as well as its shape and connectability with other components, permits it to be secured to a patient within a small volume, or envelope, such that interoperative scans of the patient can be taken without disconnecting the retractor arm, the halo-style retractor or any of the supporting components. Further, substantially all of those components are radiolucent; and therefore, resulting images are almost free of any artifacts from such equipment.

Second, the application of male coupling members 44, 46 to the respective convex surfaces 40, 42 of the respective fixed and movable members 32, 34 substantially simplifies the process of molding the fixed and movable members 32, 34 and thus, helps to reduce the cost of manufacturing the members 32, 34.

As earlier described, the movable element has a slightly shorter width and is resiliently stretched when the locking shaft 76 is tightened. Such a construction permits the movable member to be controlled by loosening a single locking shaft 76. Further, as the locking shaft 76 is loosened, the forces applied on the starburst connectors 58, 62, 66, 60 by the resilient movable member 34 permits the movable member to be accurately adjusted from one tooth on the starbursts to another. The resiliency of the movable member 34 allows the surgeon to "feel" the motion of the movable member 34 as it "clicks" or "snaps" from one starburst tooth to another. That feature in combination with the single locking shaft 76 makes the surgical retractor 20 substantially easier to use than known halo-style retractors.

In addition, the capability of being able to adjust and lock the movable member 34 with respect to the fixed member 32 is accomplished with only one additional part, the locking shaft 76. This reduction in parts from known halo-style retractors also helps to reduce the manufacturing cost and provides a more reliable and trouble free operation.

While the invention has been illustrated by the description of one embodiment and while the embodiment has been described in considerable detail, there is no intention to restrict nor in any way limit the scope of the appended claims to such detail. Additional advantages and modifications will readily appear to those who are skilled in the art. For example, the leg 48 and locking member 50 of FIG. 4 have a substantially T-shaped cross-sectional profile. As will be appreciated, in other embodiments, the cross-sectional profile of the male couplings 44, 46 can have other shapes, for example, an L-shape, a dovetail shape, etc. In another embodiment, the locking member 50 can have a circular cross-sectional profile.

Therefore, the invention in its broadest aspects is not limited to the specific details shown and described. Consequently, departures may be made from the details described herein without departing from the spirit and scope of the claims which follow.

What is claimed is:

1. A halo retractor comprising:
a curvilinear fixed member comprising
first and second ends, and
a first male coupling projecting radially outward from the curvilinear fixed member and adapted to receive a female coupling portion of a retractor arm, the first male coupling comprising a first leg member and a first locking member, the first leg member extending over a length of the fixed member and the first leg member comprising
an inner end connected to the fixed member, and
a distal end connected to the first locking member;
a curvilinear movable member comprising
first and second ends, and a second male coupling projecting radially outward from the curvilinear movable member and adapted to receive a female coupling of a retractor arm, the second male coupling comprising a second leg member and a second locking member, the second leg member extending over a length of the movable member and the second leg member comprising an inner end connected to the movable member and a distal end connected to the second locking member;
a first pin fixed in one of the first ends and extending into an other of the first ends to rotatably connect the first ends together; and
a locking shaft extending through one of the second ends and threaded into an other of the second ends, the locking shaft operable to lock the fixed and movable members in a desired relative orientation.

2. A radiolucent halo retractor comprising:
a radiolucent curvilinear fixed member comprising
first and second ends,
a first convex surface, and
a first radiolucent male coupling projecting outward from the first convex surface and adapted to receive a female coupling portion of a retractor arm, the first radiolucent male coupling comprising a first leg member and a first locking member, the first leg member extending over a length of the first convex surface and the first leg member comprising an inner end fixed to the first convex surface and a distal end connected to the first locking member;
a radiolucent curvilinear movable member comprising
first and second ends,
a second convex surface, and
a second radiolucent male coupling projecting outward from the second convex surface of the movable member, the second radiolucent male coupling comprising a second leg member and a second locking member, the second leg member extending over a length of the second convex surface and the second leg member comprising an inner end fixed to the second convex surface and a distal end connected to the second locking member;
a first pin fixed to one of the first ends and extending into an other of the first ends to rotatably connect the first ends together; and
a locking shaft extending through one of the second ends and threaded into an other of the second ends, the locking shaft operable to lock the fixed and movable members in a desired relative orientation.

3. The radiolucent halo retractor of claim 2 wherein each of the first and the second radiolucent male couplings forms a channel with a respective one of the convex surfaces.

4. The radiolucent halo retractor of claim 2 wherein each of the first and the second radiolucent male couplings forms a pair of opposed channels with a respective one of the convex surfaces.

5. The radiolucent halo retractor of claim 2 wherein each of the first and the second radiolucent male couplings comprises a substantially T-shaped cross-sectional profile.

6. The radiolucent halo retractor of claim 2 wherein each of the first and second radiolucent male couplings comprises a substantially L-shaped cross-sectional profile.

7. The radiolucent halo retractor of claim 6 wherein each of the leg members and each respective locking member forms a channel with a respective one of the convex surfaces.

8. The radiolucent halo retractor of claim 7 wherein each of the leg members and a respective locking member form a substantially T-shaped coupling.

9. The radiolucent halo retractor of claim 8 wherein each leg member and a respective locking member form a pair of channels with a respective one of the convex surfaces.

10. The radiolucent halo retractor of claim 2 wherein the locking shaft is made from a radiolucent material.

11. The radiolucent halo retractor of claim 2 wherein the pin is made from a radiolucent material.

12. The radiolucent halo retractor of claim 2 wherein the fixed and movable members are substantially semicircular.

13. The radiolucent halo retractor of claim 2 further comprising a radiolucent retractor arm having a radiolucent female coupling connectable to one of the first and the second male couplings.

14. A radiolucent halo retractor comprising:
a radiolucent curvilinear fixed member comprising first and second ends;
a radiolucent curvilinear movable member comprising first and second ends;
first and second radiolucent starburst connectors disposed on the first ends of the fixed and movable members, respectively, the first and second starburst connectors securing the first ends of the fixed and movable members at a desired relative angular orientation;
third and fourth radiolucent starburst connectors disposed on the second ends of the fixed and movable members, respectively, the third and fourth starburst connectors securing the second ends of the fixed and movable members at a desired relative angular orientation;
a radiolucent pin affixed to one of the first and second starburst connectors and extending through another of the first and second starburst connectors, the pin providing an axis of rotation for the first ends of the fixed and movable members; and
a radiolucent locking shaft mounted with respect to one of the third and fourth starburst connectors and threadedly engaging another of the third and fourth starburst connectors, the locking shaft providing an axis of rotation for the second ends of the fixed and movable members.

15. The radiolucent halo retractor of claim 14 wherein each of the fixed and movable members has respective opposed convex and concave surfaces, and the first starburst connector is disposed on the concave surface of the fixed member and the second starburst is disposed on the convex surface of the movable member.

16. The radiolucent halo retractor of claim 15 wherein the third starburst connector is disposed on the convex surface of the fixed member and the fourth starburst is disposed on the concave surface of the movable member.

17. The radiolucent halo retractor of claim 16 wherein the radiolucent locking shaft is mounted with respect to the first starburst connectors on the fixed member and threadedly engages the second starburst connector on the movable member.

18. The radiolucent halo retractor of claim 17 wherein the radiolucent pin is affixed to the third starburst connector on the fixed member and extends through the fourth starburst connector.

19. The radiolucent halo retractor of claim 14 further comprising a radiolucent retractor arm connectable to one of the fixed and the movable members.

20. A radiolucent halo retractor comprising:
a radiolucent curvilinear fixed member comprising first and second ends, and
a first convex surface,
a radiolucent curvilinear movable member comprising first and second ends, and
a second convex surface,
the first and second ends of the fixed member being separated by a distance different from a distance separating the first and second ends of the movable member;
a first pin rotatably connecting one of the first ends and the second ends; and
a locking shaft rotatably connecting another of the first ends and the second ends, the locking shaft operable to lock the fixed and movable members in a desired relative orientation and upon the locking shaft locking the fixed and movable members together, the distance between the first and second ends of the fixed member becoming equal to the distance between the first and the second ends of the movable member and the first and second ends of one of the fixed member and the movable member resiliently spreading apart.

21. The radiolucent halo retractor of claim 20 wherein the first and second ends of the fixed member are separated by a distance greater than the distance separating the first and the second ends of the movable member.

22. The radiolucent halo retractor of claim 21 wherein the first and second ends of the movable member resiliently spread apart as the locking member locks the fixed and the movable members together.

23. The radiolucent halo retractor of claim 22 wherein the first and second ends of the movable member automatically move toward each other as the locking member loosens the fixed and the movable members.

24. The radiolucent halo retractor of claim 23 further comprising first and second radiolucent starburst connectors disposed on the first ends of the fixed and movable members, respectively, the first and second starburst connectors securing the first ends of the fixed and movable members at a desired relative angular orientation in response to the locking shaft locking the fixed and movable members together.

25. The radiolucent halo retractor of claim 24 wherein the first and second ends of the movable member automatically move toward each other as the locking member loosens the fixed and the movable members, the motion of the first and the second ends of the movable member permits the first and the second starburst connectors to be moved relative to each other.

26. The radiolucent halo retractor of claim 25 further comprising third and fourth radiolucent starburst connectors disposed on the second ends of the fixed and movable members, respectively, the third and fourth starburst connectors securing the second ends of the fixed and movable members at a desired relative angular orientation in response to the locking shaft locking the fixed and movable members together.

27. The radiolucent halo retractor of claim 26 wherein the first and second ends of the movable member automatically move toward each other as the locking member loosens the fixed and the movable members, the motion of the first and the second ends of the movable member permits the third and the fourth starburst connectors to be moved relative to each other.

28. A radiolucent halo retractor comprising:
a radiolucent curvilinear fixed member comprising first and second ends,
a first convex surface, and
a first radiolucent male coupling projecting outward from the first convex surface and adapted to receive a female coupling portion of a retractor arm;

a radiolucent curvilinear movable member comprising
first and second ends,
a second convex surface, and
a second radiolucent male coupling projecting outward from the second convex surface of the movable member and adapted to receive a female coupling of a retractor arm,
the first and second ends of the fixed member being separated by a distance different from a distance separating the first and second ends of the movable member;
first and second radiolucent starburst connectors disposed on the first ends of the fixed and movable members, respectively, the first and second starburst connectors securing the first ends of the fixed and movable members at a desired relative angular orientation;
third and fourth radiolucent starburst connectors disposed on the second ends of the fixed and movable members, respectively, the third and fourth starburst connectors securing the second ends of the fixed and movable members at a desired relative angular orientation;
a first pin rotatably connecting the first ends; and
a locking shaft rotatably connecting the second ends, the locking shaft operable to lock the fixed and movable members in a desired relative orientation.

29. A halo retractor comprising:
a curvilinear fixed member comprising
a first cavity disposed in a first surface of the fixed member,
a second cavity disposed in another surface of the fixed member, the second cavity intersecting with, and being substantially perpendicular to, the first cavity, and
a locking screw threaded into the fixed member and having a distal end;
a curvilinear movable member connected to, and movable with respect to, the fixed member;
a support bracket connectable to the fixed member, the support bracket comprising
a support rod being slidable through the second cavity, and
a projection on an upper end of the support rod, the projection being slidable through the first cavity but not through the second cavity, the projection being lockable in the second cavity by rotation of the locking screw; and
a mounting clamp adapted to clamp and unclamp the halo-type retractor with respect to a cranial stabilization device.

30. The halo retractor of claim 29 further comprising:
a third cavity disposed in a third surface of the curvilinear fixed member at a location substantially diametrically opposed a location of the first cavity;
a fourth cavity disposed in a fourth surface of the fixed member, the third cavity intersecting with, and being substantially perpendicular to, the fourth cavity; and
a second locking screw threaded into the fixed member and having a distal end.

* * * * *